(12) United States Patent  
Huang et al.

(10) Patent No.: US 9,339,568 B2  
(45) Date of Patent: *May 17, 2016

(54) REDUCED TEMPERATURE STERILIZATION OF STENTS

(71) Applicant: Abbott Cardiovascular Systems Inc., Santa Clara, CA (US)

(72) Inventors: Bin Huang, Pleasanton, CA (US); Abigail Freeman, Del Mar, CA (US); Daniel Castro, Mountain View, CA (US); David C. Gale, Kennesaw, GA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,952

(22) Filed: Apr. 28, 2014

(65) Prior Publication Data

US 2014/0230373 A1 Aug. 21, 2014

Related U.S. Application Data

(60) Continuation of application No. 13/906,222, filed on May 30, 2013, now Pat. No. 8,747,736, which is a division of application No. 13/179,471, filed on Jul. 8, 2011, now Pat. No. 8,475,713, which is a division of application No. 11/486,690, filed on Jul. 13, 2006, now Pat. No. 7,998,404.

(51) Int. Cl.
*A61L 2/08* (2006.01)
*B65B 55/00* (2006.01)

(Continued)

(52) U.S. Cl.
CPC . *A61L 2/08* (2013.01); *A61L 2/081* (2013.01); *A61L 2/082* (2013.01); *A61L 2/085* (2013.01); *A61L 2/087* (2013.01); *A61L 2/10* (2013.01); *B65B 55/00* (2013.01); *B65B 55/16* (2013.01);

(Continued)

(58) Field of Classification Search
CPC ... A61L 2/0029; A61L 2/0035; A61L 2/0041; A61L 2/0047; A61L 2/0058; A61L 2/007; A61L 2/08; A61L 2/081; A61L 2/082; A61L 2/085; A61L 2/087; A61L 2/10; A61L 2202/24; B65B 55/00; B65B 55/16
See application file for complete search history.

(56) References Cited

U.S. PATENT DOCUMENTS 4,983,849 A 1/1991 Thompson et al.
5,510,077 A 4/1996 Dinh et al.

(Continued)

FOREIGN PATENT DOCUMENTS

EP 0424159 4/1991
EP 1520795 4/2005

(Continued)

OTHER PUBLICATIONS

"Sterilisation of health care products-radiation-part 3: guidance on dosimetric aspects", ISO 11137-3, published Apr. 15, 2006, 30 pgs.

(Continued)

*Primary Examiner* — Regina M Yoo
(74) *Attorney, Agent, or Firm* — Squire Patton Boggs (US) LLP

(57) ABSTRACT

Methods and systems for reduced temperature radiation sterilization of stents are disclosed.

15 Claims, 8 Drawing Sheets

(51) Int. Cl.
*B65B 55/16* (2006.01)
*A61L 2/10* (2006.01)

(52) U.S. Cl.
CPC .......... *A61L 2202/23* (2013.01); *A61L 2202/24* (2013.01)

(56) References Cited

U.S. PATENT DOCUMENTS

| | | | |
|---|---|---|---|
| 5,603,972 | A | 2/1997 | McFarland |
| 6,248,129 | B1 | 6/2001 | Froix |
| 6,358,556 | B1 | 3/2002 | Ding et al. |
| 6,682,695 | B2 | 1/2004 | MacPhee et al. |
| 6,932,930 | B2 | 8/2005 | DeSimone et al. |
| 7,959,857 | B2 * | 6/2011 | Freeman et al. ............ 422/22 |
| 7,998,404 | B2 | 8/2011 | Huang et al. |
| 8,034,287 | B2 | 10/2011 | Freeman et al. |
| 8,309,022 | B2 * | 11/2012 | Huang et al. ............ 422/22 |
| 8,475,713 | B2 * | 7/2013 | Huang et al. ............ 422/22 |
| 8,747,736 | B2 * | 6/2014 | Huang et al. ............ 422/22 |
| 2004/0052284 | A1 | 3/2004 | Krause et al. |
| 2005/0003007 | A1 | 1/2005 | Boix et al. |
| 2005/0027283 | A1 | 2/2005 | Richard et al. |
| 2005/0118344 | A1 | 6/2005 | Pacetti |
| 2007/0178129 | A1 | 8/2007 | Flanagan |
| 2007/0280851 | A1 | 12/2007 | Freeman et al. |
| 2008/0010947 | A1 | 1/2008 | Huang et al. |

FOREIGN PATENT DOCUMENTS

| | | |
|---|---|---|
| JP | 3-170156 | 7/1991 |
| JP | 2006-519672 | 8/2006 |
| WO | WO 02/15725 | 2/2002 |
| WO | WO 2004/066876 | 8/2004 |
| WO | WO 2005/074619 | 8/2005 |

OTHER PUBLICATIONS

Anis et al, "The future of drug eluting stents", Heart 2006; 92: 585-588, published Oct. 10, 2005.

Htay et al, "Drug eluting stent: a review and update", Vascular Health and Risk Management 2005: 1(4) 263-276, published Dec. 2005.

Nutek, "Sensitive materials routinely processed", published Feb. 14, 2003.

Nuutinen et al, "Effect of gamma, ethylene oxide, electron beam, and plasma sterilisation on the behaviour of SR-PLLA fibres in vitro", J. Biomater. Sci. Polymer Edn, vol. 13, No. 12, pp. 1325-1336, published Apr. 2, 2002.

Nuutinen et al, "Mechanical properties and in vitro degradation of bioabsorbable self-expanding braided stents", J. Biomater. Sci. Polymer Edn, vol. 14, No. 3, pp. 255-266, published 2003.

Rogers, "Sterilisation of Polymer Healthcare Products", Smithers Rapra Technology, p. 287, published May 12, 2005.

Tyan et al, "The study of the sterilization effect of gamma ray irradiation of immobilized collagen polypropylene nonwoven fabric surfaces", J Biomed Mater Res A. Dec. 1, 2003;67(3):1033-43., published Dec. 2003.

* cited by examiner

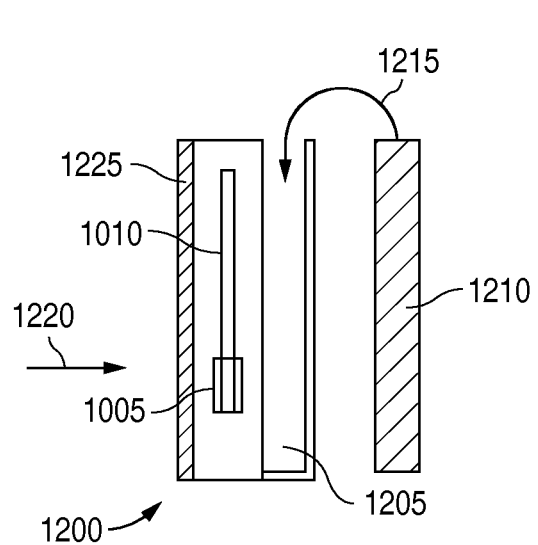
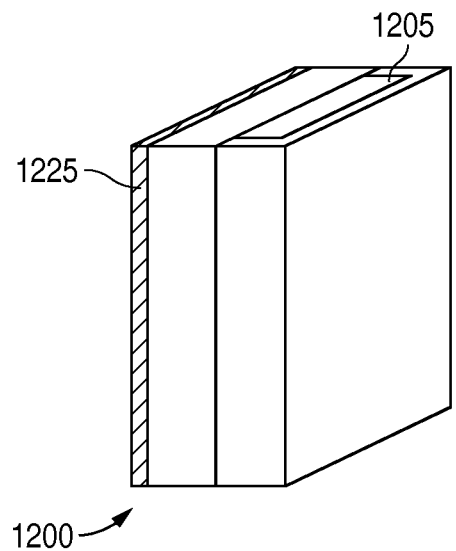
FIG. 12A  FIG. 12B
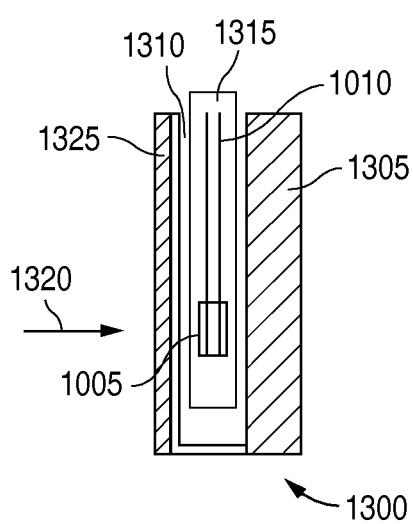
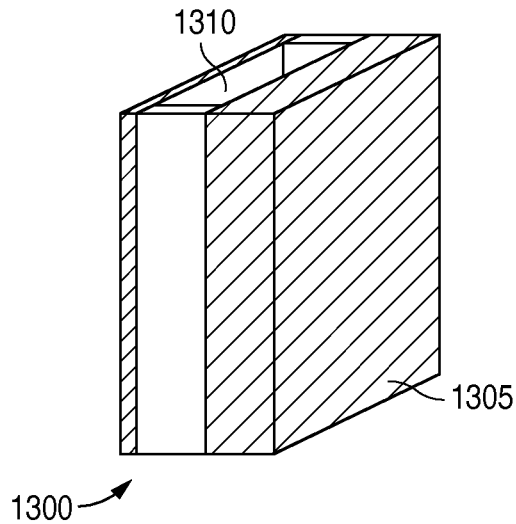
FIG. 13A  FIG. 13B

REDUCED TEMPERATURE STERILIZATION OF STENTS

This application is a Continuation of co-pending application Ser. No. 13/906,222 filed on May 30, 2013, which is a Divisional of application Ser. No. 13/179,471 filed on Jul. 8, 2011, now U.S. Pat. No. 8,475,713, issued Jul. 2, 2013, which is a Divisional of application Ser. No. 11/486,690 filed Jul. 13, 2006, now U.S. Pat. No. 7,998,404, issued Aug. 16, 2011, the entire contents of which are hereby incorporated by reference for all purposes.

BACKGROUND OF THE INVENTION

1. Field of the Invention

This invention relates to radiation sterilization of stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

After a stent is fabricated, a stent typically undergoes sterilization to reduce the bioburden of the stent to an acceptable sterility assurance level (SAL). There are numerous methods of sterilizing medical devices such as stents, the most common being ethylene oxide treatment and treatment with ionization radiation such as electron beam and gamma radiation. Generally, it is desirable for the sterilization procedure to have little or no adverse affects on the material properties of the stent.

SUMMARY

Certain embodiments of the present invention are directed to a method of sterilizing a stent comprising: cooling a stent to a sterilization temperature below ambient temperature; and exposing the cooled stent to a dose of radiation.

Additional embodiments of the present invention are directed to a method of sterilizing a stent comprising: cooling a stent to a sterilization temperature below ambient temperature; exposing the stent to a dose of radiation; and cooling the stent during the exposure to maintain the temperature of the stent during exposure at less than a selected temperature.

Further embodiments of the present invention are directed to a system for packaging a stent comprising: a container capable of storing a stent; a stent disposed within the container; and a cold medium disposed within the container adjacent to the stent, the cold media capable of reducing and maintaining the temperature of the stent below ambient temperature.

Some embodiments of the present invention are directed to a method for packaging a stent comprising: disposing a stent in a container for storing the stent, wherein a cold medium is disposed within the container, the cold medium reducing and maintaining the temperature of the stent below ambient temperature; and exposing the stent to a dose of radiation to sterilize the stent.

Additional embodiments of the present invention are directed to a method of sterilizing a stent comprising: selectively conveying a cooling fluid at or adjacent to a stent to reduce the temperature of the stent to a sterilization temperature below an ambient temperature; and directing a dose of radiation at the cooled stent.

Other embodiments of the present invention are directed to a method of sterilizing a stent comprising: disposing a stent in a container; disposing a cooling medium adjacent to the stent to reduce and/or maintain a temperature of the stent in the container at a sterilization temperature that is below ambient temperature; and directing a dose of radiation at the container to sterilize the stent.

Further embodiments of the present invention are directed to a method of sterilizing a stent comprising: cooling a stent to a sterilization temperature below an ambient temperature; and directing a dose of radiation from a radiation source at the cooled stent, a radiation barrier between the stent and the radiation source selectively reducing the radiation exposure of the stent.

Additional embodiments of the present invention are directed to a system of sterilizing a stent comprising: a hollow ring-shaped conduit including a plurality of holes for disposing a stent; a cooling medium within the conduit for maintaining the temperature of a stent disposed through one of the holes within the conduit in a sterilization temperature range; and a radiation source capable of exposing the conduit to a dose of radiation as the conduit is translated through the radiation source, the source being capable of exposing the stent to radiation.

Further embodiments of the present invention are directed to a method of sterilizing a stent comprising: disposing a stent on or adjacent to a surface of a cooling member, wherein the cooling member maintains a temperature of the stent at a sterilization temperature below ambient temperature before, during, and/or after exposing the stent to radiation; and directing a dose of radiation at the stent, the stent being positioned between the cooling slab and the radiation source.

Other embodiments of the present invention are directed to a system for sterilizing a stent comprising: a cooling member capable of maintaining a temperature of a stent at a sterilization temperature below ambient temperature before, during, and/or after exposing the stent to radiation, wherein the stent is positioned on or adjacent to a surface of the cooling member; and a radiation source for exposing the stent to radiation to sterilize the stent, the stent being positioned between the cooling member and the radiation source.

Additional embodiments of the present invention are directed to method of sterilizing a stent comprising: disposing a stent adjacent to a surface of a cooling member; conveying a cooling fluid from the surface of the cooling member, wherein the cooling fluid facilitates maintaining a temperature of the stent at a sterilization temperature below ambient temperature before, during, and/or after exposing the stent to radiation; and directing a dose of radiation at the stent, the stent being positioned between the cooling member and the radiation source.

Some embodiments of the present invention are directed to a system for sterilizing a stent comprising: a cooling member including a cooling medium disposed in cavity of the cooling medium, the surface of the cooling member having a plurality of holes in communication with the cavity, the holes for conveying a cooling fluid from the surface of the cooling member, the cooling fluid facilitating maintaining a temperature of a stent disposed at or adjacent to the surface of the cooling member at a sterilization temperature below ambient temperature before, during, and/or after exposing the stent to radiation; and a radiation source for exposing the stent to radiation, the stent being positioned between the cooling member and the radiation source.

Certain embodiments of the present invention are directed to a system for sterilizing a stent comprising: a stent disposed in a storage container, the storage container being disposed within a cavity of a body of thermal insulating material; a cold medium disposed adjacent to the storage container within the cavity to cool the stent; and a radiation source for directing radiation at the stent to sterilize the stent.

Further embodiments of the present invention are directed to a method of sterilizing a stent comprising: disposing a storage container containing a stent within a cavity of a body a thermal insulating material, wherein a cold medium is disposed adjacent to the storage container within the cavity to cool the stent; and directing radiation at the stent.

Other embodiments of the present invention are directed to a system for sterilizing a stent comprising: a stent disposed in a storage container, the container including a sealed storage region including the stent and a cooling region adjacent to the storage region, the cooling region including a cold medium for reducing and maintaining the temperature of the stent below an ambient temperature.

Further embodiments of the present invention are directed to a method of sterilizing a stent comprising: directing radiation at a stent in a storage container, the container including a sealed storage region including the stent and a cooling region adjacent to the storage region, the cooling region including a cold medium for reducing and maintaining the temperature of the stent below an ambient temperature.

Some embodiments of the present invention are directed to a system for sterilizing a stent comprising: a cooling container comprising a cooling region and a sleeve adjacent to the cooling region, the cooling region including a cold medium; and a sealed stent storage container including a stent, the container disposed in the sleeve, the cold medium reduces and maintains the temperature of the stent below an ambient temperature.

BRIEF DESCRIPTION OF THE DRAWINGS

FIG. 12A-B depict a storage container for a stent with a sleeve adapted to receive a cold medium pocket.
FIG. 13A-B depict a cold medium storage container having a cold medium region and a sleeve adapted to receive a stent storage container.

DETAILED DESCRIPTION OF THE INVENTION

Various embodiments of the present invention relate to sterilizing stents, that are made in whole or in part of polymers, with radiation at reduced temperatures. The reduced temperature of the stent tends to facilitate preservation of the material properties of the polymer in the stent during and after exposure to radiation.

The method and systems described herein may be may be applied generally to implantable medical devices. The methods and systems are particularly relevant, for reasons discussed below, to implantable medical devices having a polymeric substrate, a polymer-based coating, and/or a drug-delivery coating. A polymer-based coating may contain, for example, an active agent or drug for local administration at a diseased site. An implantable medical device may include a polymer or non-polymer substrate with a polymer-based coating.

Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

Figure 1:
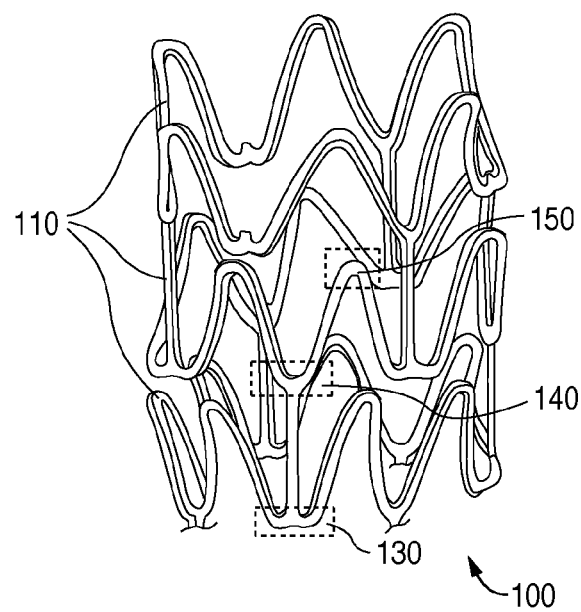
FIG. 1 depicts a stent.

The structure of a stent in particular can have a scaffolding or a substrate that includes a pattern of a plurality of interconnecting structural elements or struts. FIG. 1 depicts an example of a view of a stent 100. Stent 100 has a cylindrical shape and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

A stent has certain mechanical requirements that are crucial to successful treatment. For example, a stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Bending elements 130, 140, and 150, in particular, are subjected to a great deal of stress and strain during use of a stent.

It is well known by those skilled in the art that the mechanical properties of a polymer can be modified by applying stress to a polymer. The strength and modulus of a polymer tend to be increased along the direction of the applied stress. The application of stress can induce molecular orientation along the direction of stress which can increase the strength and modulus along the direction. Molecular orientation refers to the relative orientation of polymer chains along a longitudinal or covalent axis of the polymer chains.

Therefore, in some embodiments, a polymer tube can be radially deformed prior to laser cutting to enhance radial strength. The radial deformation increases the strength and modulus in the circumferential direction. The increase in strength and modulus can be due to the induced molecular orientation in the circumferential direction. However, as the temperature of the polymer increases close to or above Tg, some or all of the induced orientation and strength can be lost due to relaxation of polymer chains.

Sterilization is typically performed on medical devices, such as stents, to reduce the bioburden on the device. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product to be used in the body's fluid path is considered a Class III device. SAL's for various medical devices can be found in materials from the Association for the Advancement of Medical Instrumentation (AAMI) in Arlington, Va.

Radiation sterilization is well known to those of ordinary skill the art. Medical devices composed in whole or in part of polymers can be sterilized by various kinds of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes.

However, it is known that radiation can alter the properties of the polymers being treated by the radiation. High-energy radiation tends to produce ionization and excitation in polymer molecules. These energy-rich species undergo dissociation, abstraction, and addition reactions in a sequence leading to chemical stability. The stabilization process can occur during, immediately after, or even days, weeks, or months after irradiation which often results in physical and chemical cross-linking or chain scission. Resultant physical changes can include embrittlement, discoloration, odor generation, stiffening, and softening, among others.

In particular, the deterioration of the performance of polymeric materials and drugs due to e-beam radiation sterilization has been associated with free radical formation in a device during radiation exposure and by reaction with other parts of the polymer chains. The reaction is dependent on e-beam dose and level of temperature.

Additionally, exposure to radiation, such as e-beam can cause a rise in temperature of an irradiated polymer sample. The rise in temperature is dependent on the level of exposure. It has been observed that a stent-catheter assembly can increase about 7° C. per 12 kGy of radiation exposure. Mechanical properties of polymers are particularly sensitive to changes in temperature. In particular, the effect on properties becomes more profound as the temperature approaches and surpasses the glass transition temperature, Tg. It has been observed that e-beam radiation of polymer stents can result in cracking of struts during deployment due to onset of brittle behavior. The cracking can be due to the increase in temperature, as well as the reduction in molecular weight. Additionally, the increase in temperature can result in a loss of some or all of the induced orientation and strength due to relaxation of polymer chains.

Furthermore, the increase in temperature can also increase the release rate of drug resulting in a decrease of drug loading on a stent. Drugs can also degrade at increased temperatures during manufacture and storage conditions, altering the total content and release rate of the drug.

Therefore, the modification of polymer properties due to radiation is generally due the reactions which are chemical in nature as well as the increase in temperature of a sample. Thus, it is believed that reducing the temperature of a polymer-containing device before, during, and after sterilization can slow down the rate of that the modification occurs which can reduce or eliminate adverse affects of radiation sterilization.

In certain embodiments, a method of sterilizing a stent can include cooling a stent to a sterilization temperature (Ts) which is below an ambient temperature prior to exposing the stent to radiation. Ambient temperature can refer to a temperatures in a range between about 15° C. and 30° C. The cooled stent can then be exposed to a selected dose of radiation from a radiation source.

The Ts can be, for example, less than ambient temperature, ambient temperature, or the Tg of the polymer. In various embodiments, Ts can be less than 10° C., 0° C., −15° C., −25° C., −40° C., −70° C., −100° C., −150° C., −200° C., −240° C., or less than −270° C.

The dose can be selected to be sufficient to sterilize the stent to a desired degree. As indicated above, the exposure can be in one or more passes through a radiation source. In some embodiments, Ts can be selected so that the temperature of the stent after exposure to radiation is less than a selected temperature, for, example ambient temperature, 40° C. below the Tg of the polymer, 20° C. below the Tg of the polymer, 10° C. below the Tg of the polymer, or the Tg of the polymer.

In embodiments where the stent is sterilized in more than one pass through a radiation source, the stent may be cooled prior to the first pass, but not after the other passes. Alternatively, the stent can be cooled after each pass or only after some of the passes. In cases in which the stent is cooled after a pass, the stent can be cooled to Ts, below Ts, or to a temperature between Ts and the temperature of the stent at the end of the pass.

The stent can be cooled to Ts prior to sterilization in a variety of ways, including, but not limited to, cooling the stent in a freezer, blowing a cold gas on the stent, placing the stent in proximity to a cold medium such as ice, dry ice, freezable gel, liquid nitrogen, etc. Various particular embodiments of cooling a stent prior to sterilization are described herein.

In certain embodiments, a stent an also be cooled during exposure to radiation sterilization. In one embodiment, the stent can be cooled so that the temperature during sterilization, Tds, can be maintained at or near the sterilization temperature, Ts. Alternatively, the stent can be cooled so that Tds is maintained in a temperature or a range of temperatures between Ts and the ambient temperature. Additionally, the stent can be cooled so that Tds is less than a temperature that is above ambient temperature, for example, 40° C. below the Tg of the polymer, 20° C. below the Tg of the polymer, 10° C. below the Tg of the polymer, or the Tg of the polymer.

Figure 2:
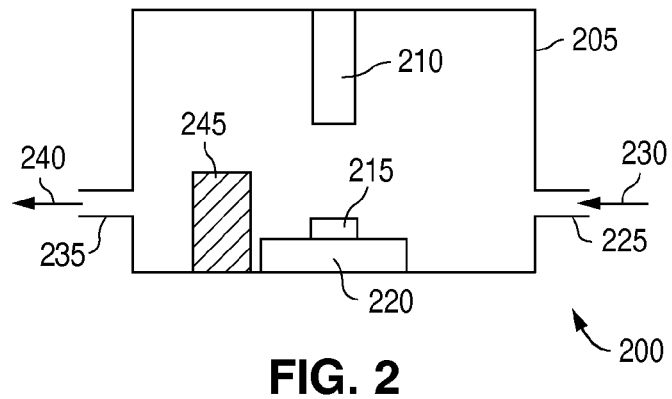
FIG. 2 depicts a radiation sterilization system.

A stent can be cooled during radiation sterilization by introducing a cold medium into a radiation chamber, such as, but not limited to, cold air, nitrogen gas, liquid nitrogen, ice, a freezable gel, or dry ice. FIG. 2 depicts a radiation sterilization system 200 including a radiation chamber 205. Radiation chamber 205 has a radiation source 210 for irradiating a stent 215 disposed on a support 220. A cooling fluid is conveyed into an inlet 225, as shown by an arrow 230. The cooling fluid can reduce and/or maintain the temperature of the stent below a sterilization temperature. The cooling fluid can exit chamber 205 through an outlet 235, as shown by an arrow 240. In addition to or as an alternative to the cooling fluid, a cold medium 245, such as dry ice or ice, can be disposed within chamber 205. Additionally or alternatively, the chamber can include a coil containing a circulating cooling fluid such as liquid nitrogen. Various other embodiments of cooling a stent during radiation sterilization are disclosed herein.

In further embodiments, a stent can be disposed in a container or package having a cold medium incorporated into the container or package. The cold medium can cool or maintain a reduced temperature of the stent before, during, or after radiation sterilization. The cold medium can also cool the stent during storage and transport of the stent. The temperature of the stent before, during, or after sterilization can be different from the temperature during storage, Tstor. For example, Tstor can be higher than a sterilization temperature.

Figure 3:
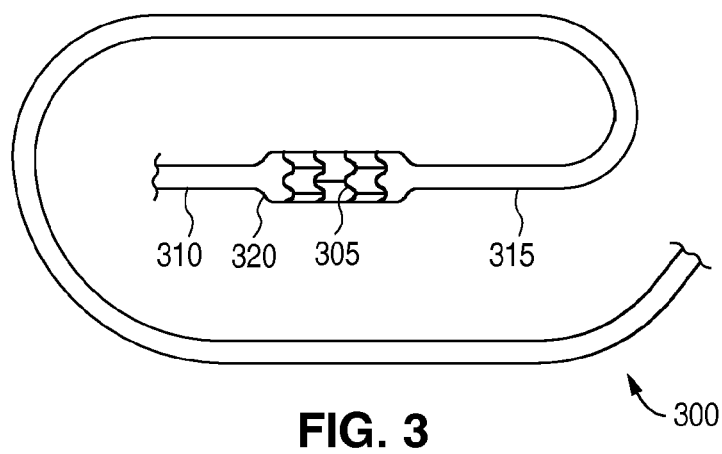
FIG. 3 depicts a stent-catheter assembly.

Stents are typically sterilized, packaged, stored, and transported in a "ready to implant" configuration in which the stent is disposed at the distal end of a catheter. FIG. 3 depicts a stent-catheter assembly 300 with a stent 305 disposed on a distal end 310 of a catheter 315. Stent 305 can be crimped over a balloon 320. The stent-catheter system 300 can be packaged prior to or after radiation sterilization.

The throughput and efficiency of a radiation sterilization process can be improved by locally or selectively cooling a stent. In general, selective cooling involves selectively cooling a stent and a small region around a stent rather than placing the stent in a large cooled environment such as a freezer. For example, the region can have a diameter less than the length of a stent, less than two times the length of a stent, less than four times the length of a stent, less than six times the length of a stent, or less than 10 times the length of a stent. The smaller mass of a stent allows the stent to be cooled relatively quickly. The reduced temperature is also more easily maintained by such selective or local cooling. Thus, selective cooling makes a large freezer for handling a large production capacity of stents unnecessary.

Figure 4A:
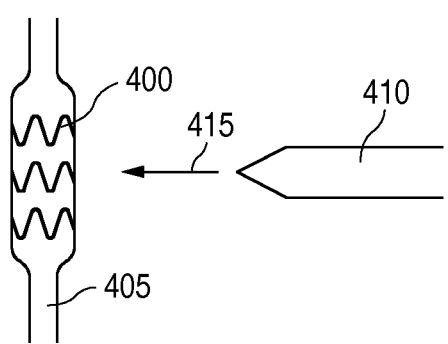
FIGS. 4A-C depict embodiments for selective cooling of a stent.

There are numerous ways of selectively cooling or reducing the temperature of a stent. In one embodiment, a stent can be cooled to a Ts by selectively conveying a fluid at a reduced temperature at or adjacent to a stent. FIG. 4A depicts a stent 400 disposed on a catheter 405. A nozzle 410 blows a cold gas selectively at stent 400, as shown by an arrow 415. The cold gas can be, for example, air, nitrogen, argon, etc. The stent can be cooled to a Ts prior to sterilization or between sterilization passes by the cold gas and then radiation sterilized. The temperature can be at a temperature at or below the Ts.

Figure 4B:
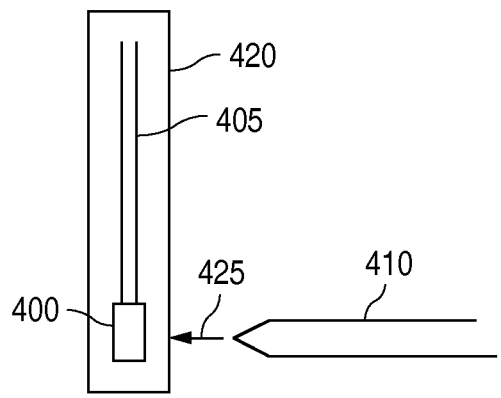

In an embodiment, as depicted in FIG. 4B, stent 400 can be inside of a storage container 420. The container, as describe below, can be a any convenient form, shape, and size to store a stent, for example, a flexible pouch made from a polymer, glass, ceramic, metallic substance, or a combination thereof. Nozzle 410 blows cold gas, as shown by an arrow 425, at container 420 where stent 400 is located.

In another embodiment, a stent can be disposed in a container that is approximately large enough to store the stent. The container can be of a size that all or a majority of the catheter cannot fit inside of the container. For example, the length and width of a container can be less than 15 times, 10 times, 7 times, 5 times, or, more narrowly, less than 2 times the length of the stent. A cooling medium can be conveyed or disposed in the container to reduce or maintain a temperature of the stent at a Ts.

Figure 4C:
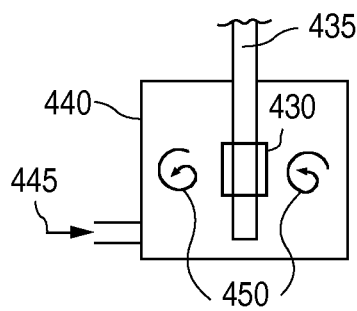

After cooling the stent to the Ts, the stent can then be exposed to radiation to sterilize the stent. The cooled stent can be removed from the container and exposed to radiation or exposed to radiation while within the container. FIG. 4C depicts a stent 430 disposed on a catheter 435 positioned within a container 440. A cold gas is conveyed, as shown by an arrow 445, and circulated within, as shown by arrows 450, container 440. Container 4C can be made from metal, foam, plastic etc. Stent 430 can be exposed to radiation. In this case, it may be desirable to make the container from a material that can reduce the dose of radiation received by the stent. The reduction in dose can be controlled by the thickness of the walls of the container. In addition, a material can be used that results in a more even distribution of radiation over a given area. For example, a material with micro-voids, such as foam, or particles can scatter e-beam radiation which results in the more even distribution. "Foam" can refer to a polymer foam, for example, polystyrene foam such as Styrofoam from Dow Chemical Company, Midland, Mich. Thus, the container material can also be made of a material that distributes radiation more uniformly such as foam.

In certain embodiments, the dose of radiation received by a stent can be selectively reduced compared to the dose received by the entire assembly. The processing of a stent may introduce a lower level of bioburden on the stent compared to the catheter. For example, the stent can be protected by a sheath during certain processing steps. Therefore, the stent may require a lower dose or radiation to effectively sterilize the stent. A reduced dose is advantageous since it will result in a reduced modification of stent properties. Additionally, the uniformity of the dose received over a stent as compared to the entire assembly can also be selectively increased.

In some embodiments, a radiation barrier can be selectively disposed between a stent cooled to a Ts and directed radiation. The barrier can selectively reduce the radiation exposure of the stent. The barrier can also selectively increase the uniformity of the dose received over the stent. The barrier can be a material such as foam which is translucent to the directed radiation. For example, the wall of container 440 in FIG. 4C can selectively reduce the radiation from a radiation source and selectively increase the uniformity of radiation exposure within the container.

In another embodiment, a stent on a stent-catheter assembly can be enclosed in a sheath during radiation sterilization. The barrier can selectively reduce the radiation exposure of the stent and increase the uniformity of the dose received over the stent. In some embodiments, the sheath can be enclosed in an additional layer of tubing to further reduce exposure and increase dose uniformity. The end of the sheath may be designed to be closed to protect the stent from bioburden loading. Alternatively, the end may be open to allow for cooling of the stent. In another embodiment, a pocket can be disposed around the stent. The sheath, tubing, or pocket can be composed of a polymer, metal, or a combination thereof.

Figure 5A:
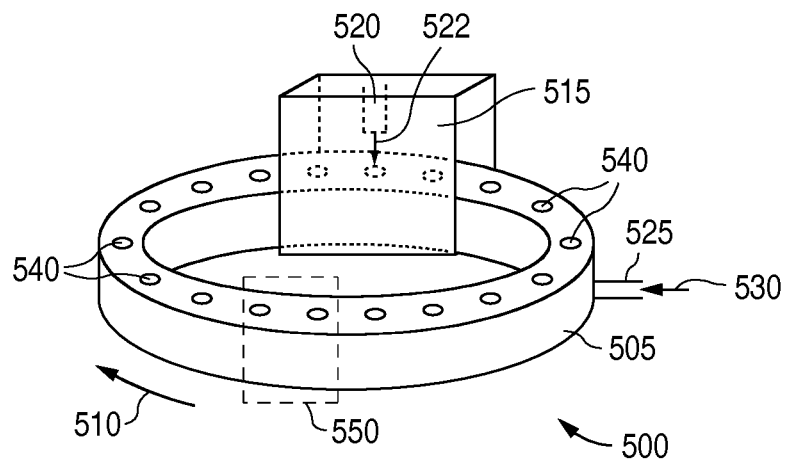
FIGS. 5A-D depict an exemplary embodiment of a system for reduced temperature radiation sterilization of a stent.
Figure 5B:
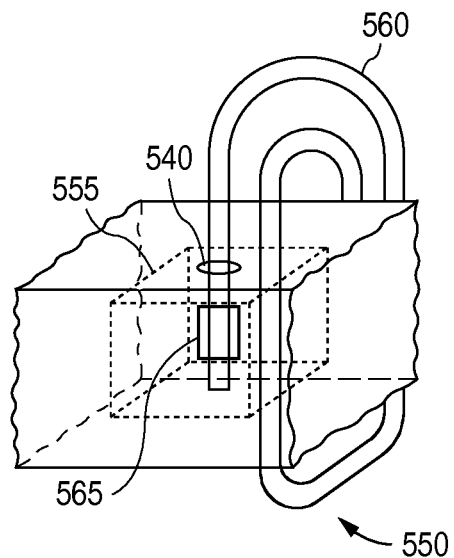
Figure 5C:
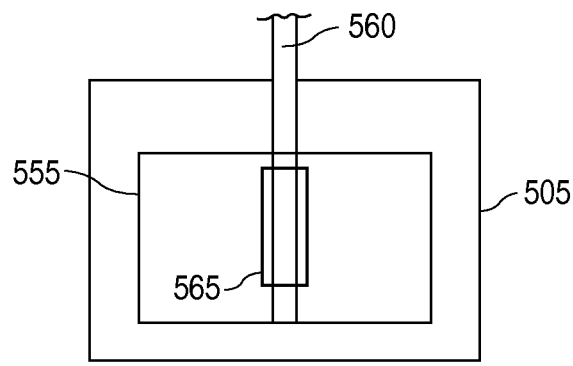

Some embodiments of reduced temperature radiation sterilization can include a continuous process that allows one or more passes of radiation exposure. Such embodiments can incorporate selective cooling of the stent and selective reduction of radiation dose on the stent. FIGS. 5A-C depict an exemplary system 500 for radiation sterilization of stents. System 500 includes a hollow, ring-shaped conduit 505 that is adapted to rotate, as shown by an arrow 510. Conduit 505 can be rotated, for example, by a conveyer belt system (not shown). As conduit 505 rotates it passes through a radiation chamber 515 that has a radiation source 520 that can direct radiation onto conduit 505, as shown by an arrow 522. Conduit 505 has an inlet 525 for a cooling gas which is conveyed into conduit 505, as shown by an arrow 530.

Conduit 505 has a plurality of holes 540 along a top surface of conduit 505. Holes 540 are in communication with a plurality of containers 545 disposed within conduit 505. Holes 505 are of a size to accommodate a catheter and stent disposed on a catheter. FIG. 5B depicts a cutout section 550 from FIG. 5A showing the interior of conduit 505. FIG. 5B shows a container 555 disposed within conduit 505. A distal end of a catheter 560 is disposed through hole 540 and within container 555. The container can be of a size that all or a majority of the catheter cannot fit inside of the container. A stent 565 is disposed on the distal end of catheter 560. FIG. 5C depicts a cross-sectional view down the axis of conduit 505 showing container 555. The container can be made of materials including, but not limited to, foam, metal, and plastics. The conduit can be made of materials including, but not limited to, foam, metal, and plastics.

One more of sections with holes 540 can have a stent-catheter system with a stent 565 disposed within a container 555. As conduit 505 rotates, a stent-catheter assembly is radiation sterilized as it passes through radiation chamber 525. Conduit 505 can rotate continuously at a constant or near constant rate. Alternatively, conduit 505 can rotate in discrete steps. Radiation source 520 directs radiation through container 444 and onto stent 565. A plurality of stent-catheter assemblies can be radiation sterilized using system 500 as conduit 505 rotates. A stent-catheter assembly can be passed through radiation chamber 525 one or more times. Additionally, the walls of conduit 555 can act as a barrier can selectively reduce the radiation exposure of the stent, as described above.

During a radiation sterilization run, cooling gas circulates through conduit 505 and cools stents 565. Therefore, stents 565 are cooled prior to, during, and after exposure to radiation in radiation chamber 515. The temperature of stents 565 can be maintained within a selected Ts range. It is expected that the temperature of a stent 565 will be the greatest immediately after exposure and the lowest just prior to exposure to radiation. The cooling of the stent can be adjusted so that the temperature of the stent just prior to exposure to radiation is at a selected Ts. The cooling of the stent can be adjusted by the flow rate of cooling gas, the temperature of the cooling gas, and the rate of rotation of conduit 505.

Figure 5D:
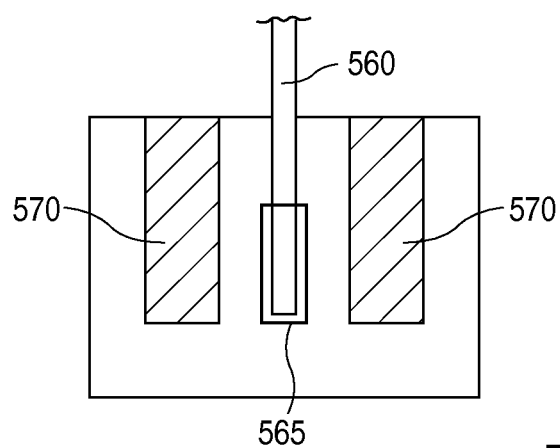

FIG. 5D depicts an alternate embodiment for the interior of conduit 505. Interior cooling conduits 570 are positioned on either side of a stent 565 disposed within conduit 505. A cooling fluid disposed within cooling conduits 570 selectively cools stent 565. The cooling fluid can be a gas or a liquid coolant such as liquid nitrogen.

Further embodiments of reduced temperature radiation sterilization of a stent can include disposing a stent on or adjacent to a surface of a cooling member such as a plate or slab. The cooling member can reduce and maintain a temperature of the stent at a Ts below ambient temperature before, during, and/or after exposing the stent to radiation. The stent can be positioned between a radiation source and the cooling member.

Figure 6A:
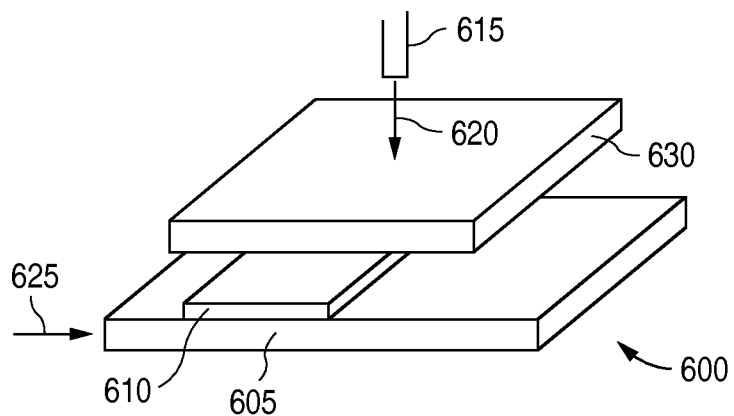
FIGS. 6A-C depict an exemplary embodiment of a system for reduced temperature radiation sterilization of a stent.

FIG. 6A depicts an exemplary embodiment a system 600 for reduced temperature radiation sterilization of a stent. System 600 includes a cooling slab or plate 605. A support 610 for supporting a stent is disposed on the surface of cooling plate 605. A cooling medium within cooling plate 605 maintains the temperature of the surface of cooling plate 605 at a reduced temperature. Cooling plate 605 reduces and maintains the temperature of a stent disposed on support 610 at a reduced temperature prior to, during, and/or after radiation sterilization. Cooling plat 605 and support 610 can be made of metal, plastic, foam, etc.

A radiation source 615 directs radiation onto a stent, as shown by an arrow 620, disposed on support 610. Cooling plate 605 can be adapted to translate in the direction shown by an arrow 625 so that a stent disposed on support 610 is positioned beneath radiation source 615. A barrier 630 can be positioned between radiation source 615 and the stent disposed on support 610. Barrier 630 can be a foam or other materials including metals and plastics, that distributes the radiation, such as e-beam, more uniformly so that there is a more uniform exposure on the stent and a catheter on which a stent is disposed. Additionally, barrier 630 can also reduce the dose of the radiation directed from radiation source 615.

Figure 6B:
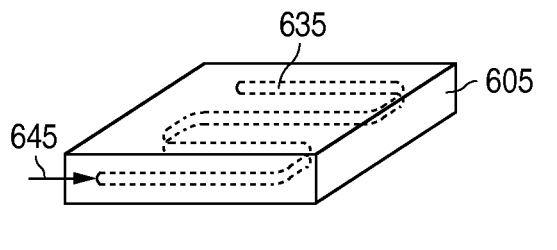
Figure 6C:
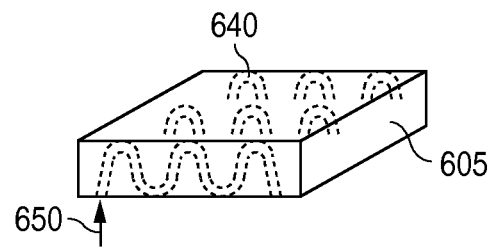

Cooling plate 605 can be cooled by disposing a cooling medium within cooling plate 605. For example, FIGS. 6B-C depict the interior of cooling plate 605 showing cooling coils 635 and 640, respectively. A cooling fluid enters coils 635 and 640, as shown by arrows 645 and 650.

Figure 7:
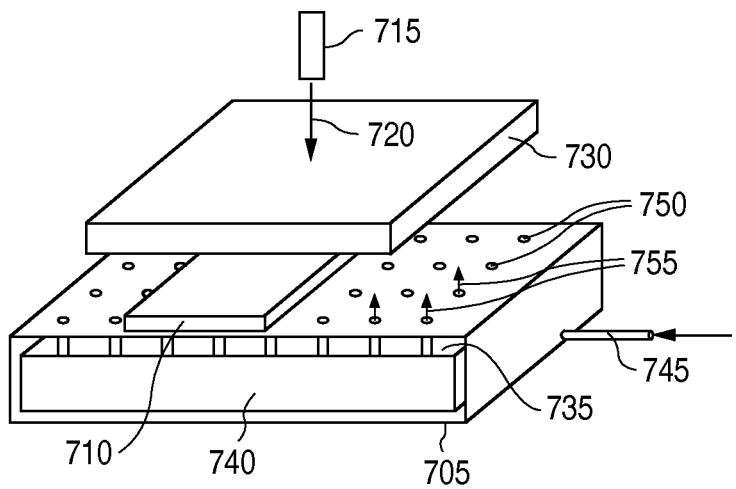
FIG. 7 depicts an exemplary embodiment of a system for reduced temperature radiation sterilization of a stent.

FIG. 7 depicts a convection cooling system 700 in which a stent is at least partially cooled by convection for radiation sterilization. Similar to system 600 in FIG. 6A, system 700 includes a cooling slab 705, a support 710 for a stent to be sterilized, a barrier 730, and a radiation source 715 that directs radiation, as shown by an arrow 720. Cooling slab 705 has a cavity 735 of which a majority is filled with a cooling medium 740. Cooling medium 740 can be, for example, dry ice, freezable gel, ice, or coils with a circulating fluid such as liquid nitrogen. A cooling gas, such as air, nitrogen, or argon, can be blown into an inlet 745 to cavity 705. The temperature of the cooling gas is reduced as it circulates through and around cooling medium 740. The reduced temperature cooling gas exits through a plurality of holes 750, as shown by arrows 755, and provides convection cooling of the stent disposed on support 710. The stent is also partially cooled by conduction through cooling slab 705. The degree of cooling, and thus the temperature of the stent can be adjusted by the flow rate of cooling gas and the temperature of cooling medium 740.

Figure 8:
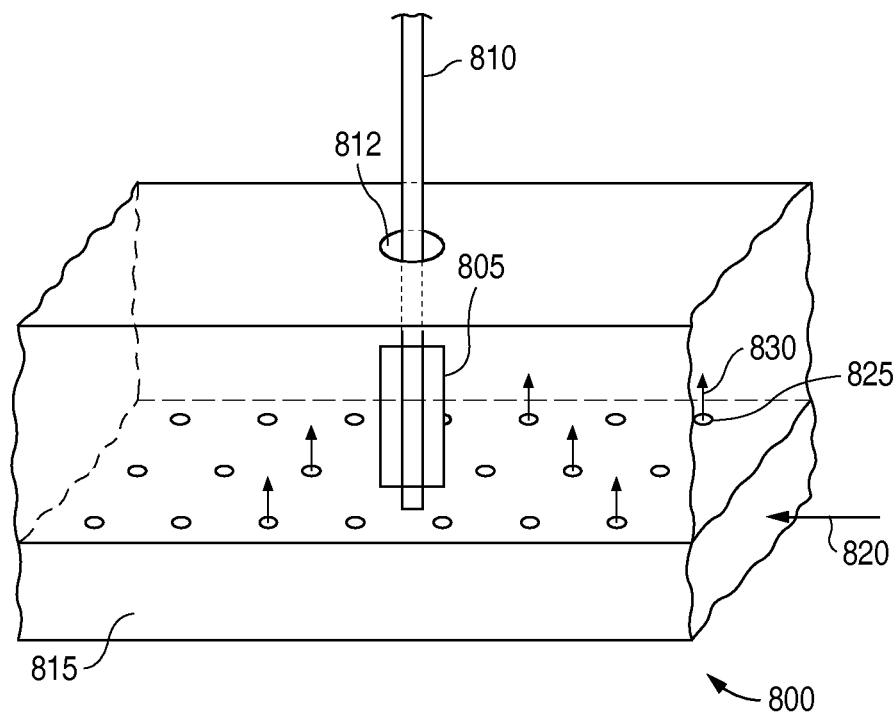
FIG. 8 depicts an exemplary section of the conduit from FIG. 5A.

The exemplary embodiments in FIGS. 6A-C and 7 can also be adapted to selective cooling of the stent. FIG. 8 depicts a section 800 of conduit 505 from FIG. 5A. A stent 805 is disposed on a catheter 810 disposed through hole 812 and within conduit 505. Conduit 505 has a cooling slab 815 below stent 805. The interior of cooling slab 815 can have a cooling medium as in FIG. 6B or 6C with coils that have a circulating cooling fluid. Alternatively, the cooling medium can be similar to FIG. 7 with cooling gas circulating, as shown by an arrow 820. The surface of cooling slab 815 can have a plurality of holes 825 through which the circulating cooling gas passes, as shown by arrows 830, which provides convection cooling of stent 805.

The temperature of a stent stored at or near a selected sterilization temperature can increase in a relatively short period of time once it is removed from a cold environment, such as a freezer. Because there is very little mass and a high surface area in a stent-catheter assembly, it transitions from its cold state quickly. For example, a stent can transition from −15° C. (freezer temperature) to 0° C. and higher within minutes. Since there is typically set-up and loading time for radiation exposure after removal of a stent from a freezer, the temperature of the stent can increase substantially before exposure to radiation.

Thus, further embodiments of reduced temperature radiation sterilization can include systems and methods for cooling a stent disposed in a storage container. Stents or stent-catheter assemblies are typically stored and transported in sealed storage containers. Such containers are adapted to protect the stent from environmental exposure (humidity, oxygen, light, etc.) which can have an adverse effect on the stent.

A storage container for a stent can be designed in any convenient form or shape that permits the effective enclosure of a stent contained therein. The container, however, should be compact and shaped so as to minimize storage space occupied by the container. For example, without limitation, the container can be in the shape of a tube, box or a pouch. In one commercially useful embodiment, container 210 can have a rectangular cross-section with a width between 8 in and 12 in and a length between 10 in and 13 in. Also, depending on the types of substance(s) used to construct the container, the container can be of various degrees of rigidity or flexibility. The container can be constructed of flexible films rather than rigid materials because it is less likely that the seal would be compromised by a change in atmospheric conditions during storage. For example, the container can be constructed of two sheets or lamina which have been joined along an edge. Also, the container can be constructed of a single sheet or lamina which has been folded and sealed along all edges or along all non-fold edges; or a bag or pocket which is sealed along one or more edges. The pouches can be made from a polymer, glass, ceramic, metallic substance, or a combination thereof. Typically, the pouches are made of metallic foil.

Such containers can be stored individually or stored together with other packaged stents. For example, a pouch can be disposed in a box, such as chipboard box. The chipboard box can then be stored individually or along with a number of similar or identical containers including stents.

Embodiments of radiation sterilization of stents can include systems and methods of cooling stents within the above-described or other storage containers. In some embodiments, a cooling medium can be incorporated or positioned adjacent to the stent within a storage container. The system can be used to reduce and maintain a selected Ts of a stent prior to, during, and/or after radiation sterilization.

In some embodiments, a storage container including a stent can be disposed within a cavity of an insulating material, such as foam. A cold medium can be positioned adjacent to the storage container within the cavity to cool the stent. The cold medium or the container can be positioned to maximize the cooling of the stent. The stent can be sterilized by directing radiation from a radiation source in such a way that the cold medium is not between the directed radiation and the stent.

Figure 9A:
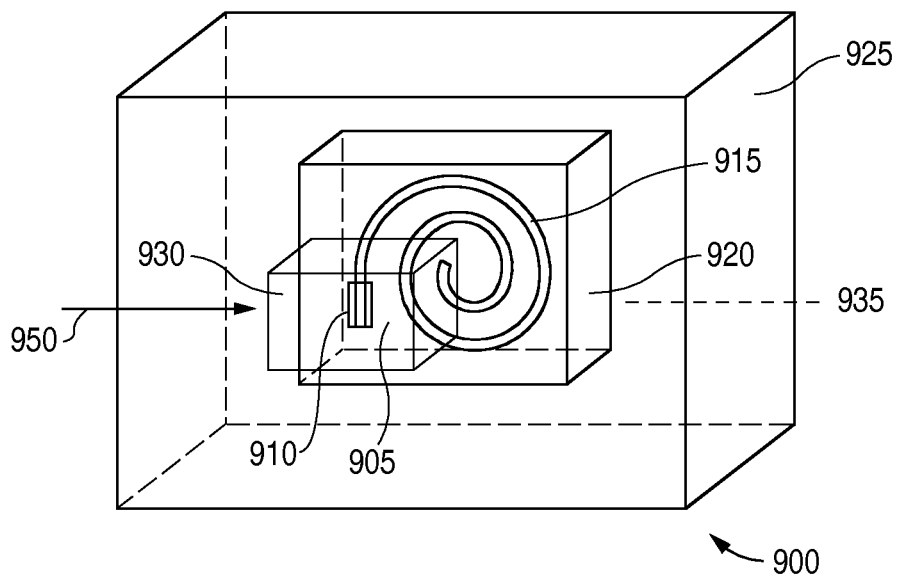
FIG. 9A-C depict an exemplary system for reduced temperature sterilization of a stent.

FIG. 9A depicts an exemplary system 900 for reduced temperature sterilization of a stent. System 900 includes stent-catheter assembly 905 with a stent 910 attached to a distal end of a catheter 915 disposed within a container 920. Container 920 can be a chipboard box or other suitable container. The stent-catheter assembly 905 can alternatively or additionally be disposed within a sealed flexible container or pouch such as one described above. Container 920 is disposed within a cavity of a block 925 of an insulating material such as foam.

In addition, a cold medium 930 is positioned in a cavity within block 925 adjacent to stent 910 to reduce and maintain the temperature of stent 910 at a selected Ts. An additional cold medium (not shown) can also be positioned on a side opposite to cold medium 930. Cold medium 930 and an addition cold medium can be positioned to maximize cooling of stent 910.

Figure 9B:
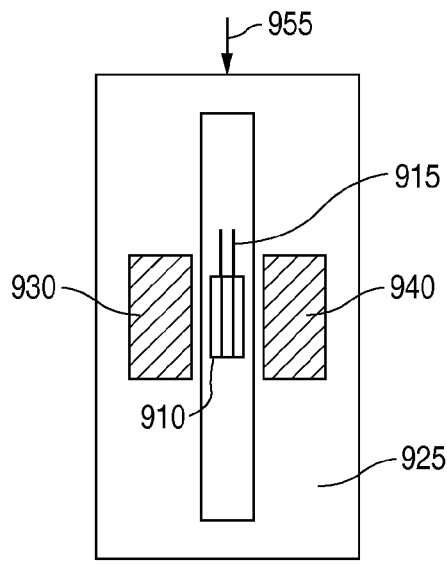
Figure 9C:
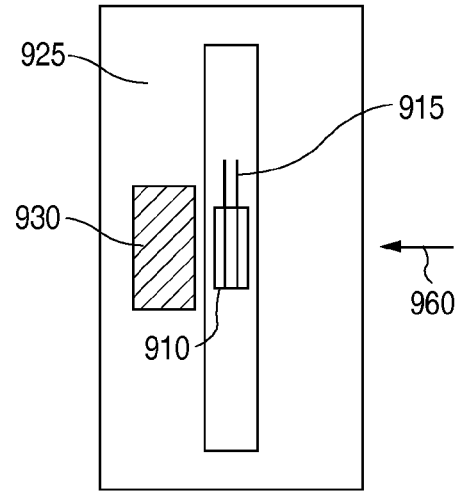

FIG. 9B depicts a cross-section of system 900 along an axis 935. FIG. 9B shows cold medium 930 on one side of stent 910 and a cold medium 940 on a side opposite to stent 910. Radiation can be directed at stent 910 so that a majority or all of radiation sterilizing the stent does not pass through cold medium 930 or 940. Thus, a radiation-source can direct radiation as shown by arrows 950 and 955. It is generally not desirable to direct radiation through cold medium 930 or 940 since the radiation can be scattered, and thus may not effectively sterilize stent 910. Alternatively, as shown in FIG. 9C, system 900 can have one cold medium 930 and no cold medium on a side opposite to stent 910. In this case, radiation can be directed as shown by an arrow 960.

System 900 can be passed through an e-beam chamber any number of times to sterilize the stent. The cold media can be replaced as necessary. Such a system eliminates the need for freezing an entire product prior to processing and between radiation passes.

Additional embodiments of reduced temperature sterilization can include a cold medium incorporated in, coupled to, attached to, or associated with a storage container for a stein. The cold medium can be a freezable gel, ice pack, or other material can maintain a stent at or near a selected Ts. In some embodiments, the cold medium can be a material that can maintain a low temperature through endothermic reactions included in the material. The cold medium, can be positioned in or on the storage container adjacent to the stent. A storage container with a cold medium can allow a stent to stay cold during transition states such as moving from the freezer to a radiation processing station and/or during transient heating during shipping.

Figure 10A:
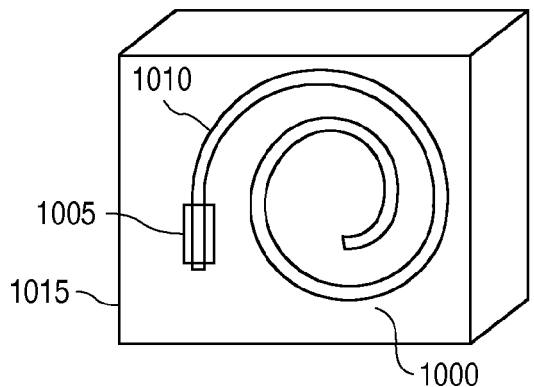
FIG. 10A-B depict a stent catheter assembly disposed in a sealed flexible storage container.
Figure 10B:
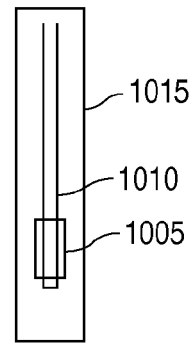

FIG. 10A depicts a front view and FIG. 10B depicts an end view of a stent catheter assembly 1000 including a stent 1005 disposed at the distal end of a catheter 1010. Stent catheter assembly 1000 is disposed in a storage container 1015, as discussed above. Storage container 1015 can be modified in various ways to incorporate a cold medium to reduce and maintain the stent temperature at or near a selected Ts.

Figure 11A:
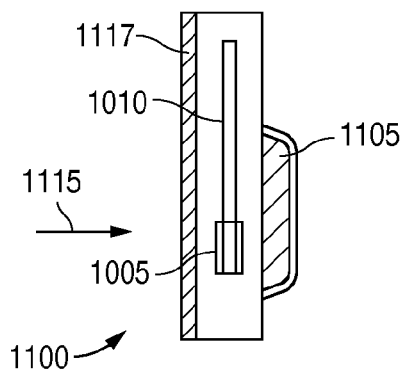
FIG. 11A-B depict a storage container for a stent that includes a cold medium pocket.
Figure 11B:
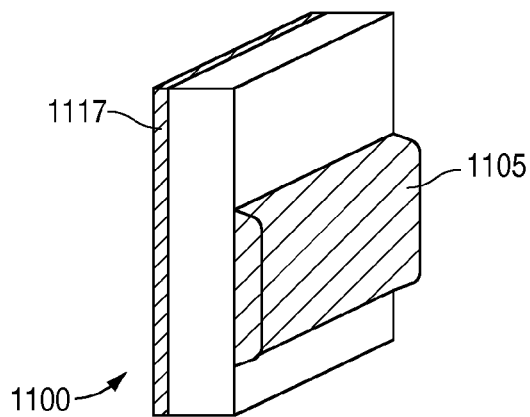

FIG. 11A depicts an end view and FIG. 11B depicts a view at an angle of a storage container 1100 modified to include a cold medium pocket 1105. Pocket 1105 can include a cold medium material that when cooled or frozen can reduce and maintain stent 1005 at a reduced temperature. Pocket 1105 can incorporated into the structure of container 1100. For example, pocket 1100 can be thermoformed onto container 1100. Thus, pocket 1105 can be made of polymer materials. Pocket 1105 can also be made of metallic materials.

Stent 1005 is disposed into container 1100 before or after the cold medium pocket 1105 has been cooled or frozen. Stent 1005 can be radiation sterilized by directing radiation as shown by an arrow 1115. Additionally, container 1100 includes barrier layer 1117 including a material to reduce radiation exposure and/or increase the uniformity of the radiation directed at the stent. Barrier layer 1117 can be, for example, foam or water.

FIG. 12A depicts an end view and FIG. 12B depicts a view at an angle of a storage container 1200 modified to include a sleeve 1205 that is adapted to receive a cold medium pocket 1210, as shown by an arrow 1215. Cold medium pocket 1210 can be cooled or frozen separately from container 1200 and disposed into sleeve 1205 to cool stent 1005. Cold medium pocket 1210 can be replaced as necessary prior to, after sterilization, or between passes or radiation exposure. Stent 1005 can be radiation sterilized by directing radiation as shown by an arrow 1220. Container 1200 includes barrier layer 1225 including a material to reduce radiation exposure and/or increase the uniformity of the radiation directed at the stent.

FIG. 13A depicts an end view and FIG. 13B depicts a view at an angle of a cold medium storage container 1300 that has a cold medium region 1305 and a sleeve 1310 adapted to receive a stent storage container 1315. Cold medium storage container 1300 can be cooled or frozen separately or together with stent storage container 1315. Stent 1005 can be radiation sterilized by directing radiation as shown by an arrow 1320. Container 1300 includes barrier layer 1325 including a material to reduce radiation exposure and/or increase the uniformity of the radiation directed at the stent.

In some embodiments, a portion of barrier layer 1117, barrier layer 1225, or barrier layer 1325 can be adapted to reduce exposure more than the rest of the barrier layer. For example, the portion can be thicker or be composed of a material that absorbs radiation to a greater degree. The portion can be of a size that allows selective increased reduction of radiation exposure of a stent. For example, the area of the portion can be approximately that of an axial cross-section of a stent or two, four, or ten times the axial cross-section of a stent. The portion can selectively increase the reduction of the radiation exposure of the stent. The portion can also selectively enhance the increase in the uniformity of the dose received over the stent.

The "glass transition temperature," Tg is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A polymer for use in fabricating an implantable medical device, such as a stent, can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate a substrate of an implantable medical device or a coating for an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

A drug or active agent can include, but is not limited to, any substance capable of exerting a therapeutic, prophylactic, or diagnostic effect. The drugs for use in the implantable medical device, such as a stent or non-load bearing scaffolding structure may be of any or a combination of a therapeutic, prophylactic, or diagnostic agent. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

A stent storage container, for example, container 1015, can be made of various substances that form a barrier when sealed. For instance, the can be made of a polymer, glass, ceramic or a metallic substance such as aluminum, stainless steel or gold. If made of a metallic substance, the container for example can be formed of a metallic film. Suitable examples of films include, but are not limited to, gold, platinum, platinum/iridium alloy, tantalum, palladium, chromium, and aluminum. Suitable materials for the container may also include oxides of the above-mentioned metals, for example, aluminum oxide. Medical storage containers may be obtained from, for example, Oliver Products Company of Grand Rapids, Mich.

Suitable polymers for construction of a stent storage container can include polymers of polyolefins, polyurethanes, cellulosics (i.e., polymers having mer units derived from cellulose), polyesters, polyamides, poly(hexamethylene isophthalamide/terephthalamide) (commercially available as Selar PA™), poly(ethylene terephthalate-co-p-oxybenzoate) (PET/PHB, e.g., copolymer having about 60-80 mole percent PHB), poly(hydroxy amide ethers), polyacrylates, polyacrylonitrile, acrylonitrile/styrene copolymer (commercially available as Lopac™), rubber-modified acrylonitrile/acrylate copolymer (commercially available as Barex™), liquid crystal polymers (LCP) (e.g. Vectra™ available from Hoescht-Celanese, Zenite™ available from DuPont, and Xydar™ available from Amoco Performance Chemicals), poly(phenylene sulfide), polystyrenes, polypropylenes, polycarbonates, epoxies composed of bisphenol A based diepoxides with amine cure, aliphatic polyketones (e.g., Carilon™ available from Shell, and Ketonex™ available from British Petroleum), polysulfones, poly(estersulfone), poly(urethane-sulfone), poly(carbonate-sulfone), poly(3-hydroxyoxetane), poly(amino ethers), gelatin, amylose, parylene-C, parylene-D, and parylene-N.

Representative polyolefins include those based upon alpha-monoolefin monomers having from about 2 to 6 carbon atoms and halogen substituted olefins, i.e., halogenated polyolefins. By way of example, and not limitation, low to high density polyethylenes, essentially unplasticized poly(vinyl chloride), poly(vinylidene chloride) (Saran™), poly(vinyl fluoride), poly(vinylidene fluoride), poly(tetrafluoroethylene) (Teflon), poly(chlorotrifluoroethylene) (Kel-F™), and mixtures thereof are suitable. Low to high density polyethylenes are generally understood to have densities of about 0.92 g cm$^{-3}$ to about 0.96 g cm$^{-3}$, however, no bright line can be drawn for density classifications and the density can vary according to the supplier.

Representative polyurethanes include polyurethanes having a glass transition temperature above a storage or ambient temperature, for example having a glass transition temperature of at least 40° C. to 60° C., or having a non-polar soft segment which includes a hydrocarbon, silicone, fluorosilicone, or mixtures thereof. For example, Elast-Eon™, manufactured by Elastomedic/CSIRO Molecular Science, is a polyurethane with a non-polar soft segment which is made from 1,4-butanediol, 4,4'-methylenediphenyl diisocyanate, and a soft segment composed of a blend of poly(hexamethylene oxide) (PHMO) and bishydroxyethoxypropylpolydimethylsiloxane (PDMS). A useful example has a blend of 20% by weight PHMO and 80% by weight PDMS.

Representative examples of cellulosics include, but are not limited to, cellulose acetate having a degree of substitution (DS) greater than about 0.8 or less than about 0.6, ethyl cellulose, cellulose nitrate, cellulose acetate butyrate, methyl cellulose, and mixtures thereof.

Representative polyesters include saturated or unsaturated polyesters such as, but not limited to, poly(butylene terephthalate), poly(ethylene 2,6-naphthalene dicarboxylate) (PEN), and poly(ethylene terephthalate).

Representative polyamides include crystalline or amorphous polyamides such as, but not limited to, nylon-6, nylon-6,6, nylon-6,9, nylon-6,10, nylon-11, aromatic nylon MXD6 (manufactured by Mitsubishi Gas Chemical America, Inc.), and mixtures thereof.

Representative polyacrylates include, but are not limited to, poly(methylmethacrylate) and polymethacrylate.

A stent storage container may also be composed of copolymers of vinyl monomers with each other and olefins such as poly(ethyl vinyl acetate).

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

The benefits of cooling a stent prior to e-beam sterilization are illustrated by the following examples. The effect of a reduced temperature e-beam radiation treatment on the number of cracks upon deployment of a poly(L-lactide) stent was investigated.

Five stent samples were radiation sterilized with e-beam radiation. The stent samples were 1.3 mm outside diameter. After radiation sterilization, each sample was then deployed or expanded to 3.5 mm. The number of cracks above 25% of the strut width and the total number of cracks at day 1 and day 7 after deployment were then counted. Four different samples were compared as shown in Table 1.

TABLE 1

Summary of samples irradiated with e-beam.

| Sample | Dose (kGy) | Number of Passes | Temperature (° C.) |
|---|---|---|---|
| 1 | 25 | 1 | −15 |
| 2 | 25 | 2 | −15 |
| 3 | 25 | 2 | Room Temperature |
| 4 | 40 | 3 | −15 |
| 5 | 40 | 1 | Room Temperature |

Figure 14:
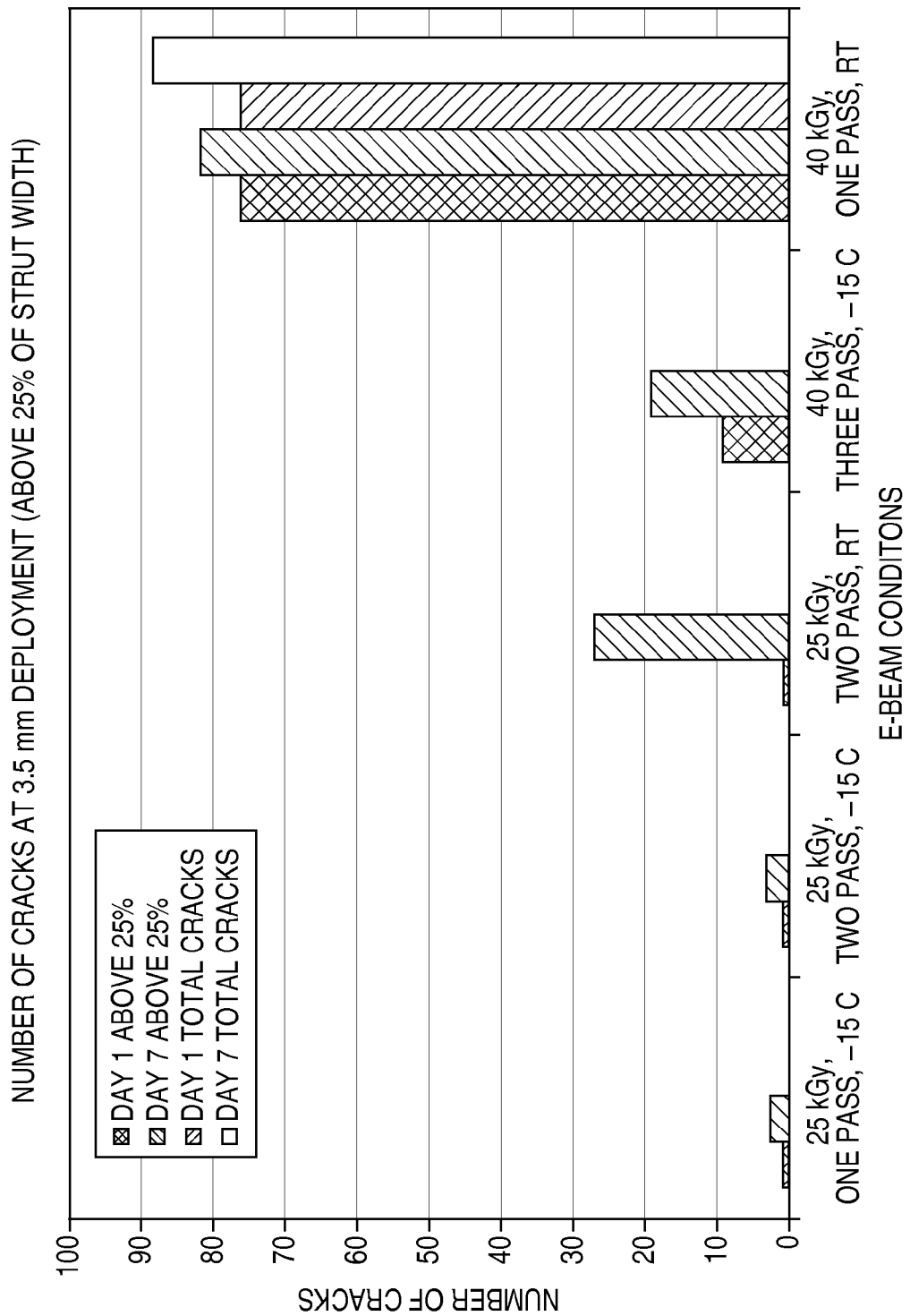
FIG. 14 is a graph depicting the number of cracks in irradiated deployed stents.

FIG. 14 depicts the number of cracks above 25% of the strut width for each of the samples at day 1 and day 7. The temperature refers to the temperature of the sample prior to e-beam sterilization. Samples 1, 2, and 4 were cooled to −15° C. prior to sterilization. The cooled samples were not cooled during or after sterilization.

Regarding samples with 25 kGy doses, the number of cracks above 25% of strut width at day 1 for the reduced temperature e-beam samples, 1 and 2, is about the same as the room temperature sterilization. However, the number of cracks at day 7 was substantially larger for the room temperature samples.

With respect to samples with 40 kGy doses, the number of cracks above 25% of strut width for the room temperature sample was substantially larger than the reduced temperature sample at both day 1 and day 7. Therefore, reduced temperature radiation sterilization substantially reduces the number of cracks in a deployed stent.

In addition, the influence of a reduced temperature e-beam radiation treatment on drug recovery was investigated. As indicated above, radiation sterilization can cause a loss of drug from a drug-containing stent. The loss can result from premature release or thermal degradation. Stent samples with a drug-polymer coating were radiation sterilized with e-beam radiation. The samples had a poly(L-lactide) substrate with a poly(DL-lactide)-drug coating. The drug was everolimus. The radiation dose was 25 kGy and the temperature of the samples was reduced to −15° C. prior to radiation exposure. The mass of the coating and amount of drug on each sample before sterilization was determined by weighing the stent samples before and after coating. The amount of drug remaining after e-beam sterilization was determined by dissolving the remaining coating in a solvent and using High Performance Liquid Chromatography to determine the amount of drug remaining. Table 2 shows the results of the drug recovery for a set of samples that have undergone reduced temperature e-beam and room temperature e-beam sterilization. The average recovery for the reduced temperature e-beam was 94.79% and 85.72% for the room temperature e-beam. Therefore, the reduced temperature improves drug delivery during e-beam sterilization.

TABLE 2

Drug recovery after e-beam sterilization.

Reduced Temperature E-Beam

| Coating weight (μg) | Drug Recovery (μg) |
|---|---|
| 216 | 93.07 |
| 218 | 95.04 |
| 214 | 96.81 |
| 217 | 95.47 |
| 217 | 93.58 |
| Ave. | 94.79 |
| Standard Deviation | 1.5 |
| % RSD | 1.59 |

Room Temperature E-Beam

| Coating weight (μg) | Drug Recovery (%) |
|---|---|
| 212 | 88.05 |
| 214 | 76.68 |
| 202 | 90.38 |
| 208 | 89.74 |
| 218 | 83.75 |
| Ave. | 85.72 |
| Standard Deviation | 5.68 |
| % RSD | 6.62 |

While particular embodiments of the present invention have been shown and described, it will be obvious to those skilled in the art that changes and modifications can be made without departing from this invention in its broader aspects.

What is claimed is:

1. A method for packaging a medical device, comprising:
   providing a stent-catheter assembly including a polymer stent crimped to a balloon of a balloon catheter;
   directing a dose of radiation at the stent-catheter assembly sufficient to satisfy a sterility assurance level (SAL); and
   reducing the temperature of the stent-catheter assembly after directing the dose of radiation at the stent-catheter assembly.

2. The method of claim 1, further including placing a barrier between the stent-catheter assembly and a radiation source, which provides the dose of radiation, wherein the barrier is made from a material having micro-voids or particles arranged to scatter radiation to provide a more uniform distribution of dose.

3. The method of claim 1, wherein the polymer stent comprises a biostable polymer, bioabsorbable polymer, biodegradable polymer, or a combination thereof.

4. The method of claim 3, wherein the bioabsorbable polymer comprises PLLA or a PLLA and PDLA blend which forms a stereocomplex.

5. The method of claim 3, wherein the bioabsorbable polymer has a glass transition temperature at least 10° C. greater than human body temperature.

6. The method of claim 1, wherein the polymer stent comprises a coating including a biostable polymer, bioabsorbable polymer, biodegradable polymer, drug, or a combination thereof.

7. The method of claim 1, wherein the radiation is selected from the group consisting of e-beam, gamma ray, ultraviolet, infra-red, ion beam, x-ray, and laser.

8. The method of claim 1, wherein the stent-catheter assembly temperature is reduced to below 0° Celsius and the bioabsorbable polymer comprises PLLA.

9. The method of claim 8, wherein the stent-catheter assembly is within a sealed, flexible pouch and the stent-catheter assembly receives the dose of radiation while contained within the sealed flexible pouch.

10. The method of claim 9, wherein the stent-catheter assembly temperature is reduced using ice, dry ice, or a freezable gel.

11. A method for packaging a medical device, comprising:
    exposing the medical device comprising a polymer stent to a dose of radiation to sterilize the stent; and
    after exposing the polymer stent to the dose of radiation, disposing the polymer stent in a container for storing the polymer stent;
    wherein a cold medium is disposed within the container, the cold medium reducing and maintaining the temperature of the polymer stent below ambient temperature.

12. The method of claim 11, wherein the cold medium reduces the temperature of the polymer stent to below 0° C.

13. The method of claim 11, wherein the cold medium is selected from the group consisting of ice, dry ice, and freezable gel.

14. The method of claim 11, wherein the polymer stent comprises a biostable polymer, bioabsorbable polymer, biodegradable polymer, or a combination thereof.

15. The method of claim 11, wherein the polymer stent comprises a coating including a biostable polymer, biodegradable polymer, drug, or a combination thereof.

* * * * *